US007367948B2

(12) United States Patent
O'Donnell et al.

(10) Patent No.: US 7,367,948 B2
(45) Date of Patent: May 6, 2008

(54) ACOUSTIC MONITORING METHOD AND SYSTEM IN LASER-INDUCED OPTICAL BREAKDOWN (LIOB)

(75) Inventors: Matthew O'Donnell, Ann Arbor, MI (US); Jing Yong Ye, Ann Arbor, MI (US); Theodore B. Norris, Dexter, MI (US); James R. Baker, Jr., Ann Arbor, MI (US); Lajos P. Balogh, Ann Arbor, MI (US); Susanne M. Milas, Ann Arbor, MI (US); Stanislav Y. Emelianov, Ann Arbor, MI (US); Kyle W. Hollman, Fenton, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 707 days.

(21) Appl. No.: 10/643,659

(22) Filed: Aug. 19, 2003

(65) Prior Publication Data

US 2004/0040379 A1    Mar. 4, 2004

Related U.S. Application Data

(60) Provisional application No. 60/407,018, filed on Aug. 29, 2002, provisional application No. 60/406,861, filed on Aug. 29, 2002.

(51) Int. Cl.
*A61B 8/00* (2006.01)
*A61B 8/12* (2006.01)
*A61B 8/14* (2006.01)
*A61B 6/00* (2006.01)
*A61H 1/00* (2006.01)

(52) U.S. Cl. .................. 600/458; 600/437; 600/438; 600/439; 600/473; 600/476; 601/2

(58) Field of Classification Search ........ 600/437–439, 600/443, 458; 601/2
See application file for complete search history.

(56) References Cited

U.S. PATENT DOCUMENTS 5,615,675 A    4/1997    O'Donnell et al.
5,732,046 A    3/1998    O'Donnell et al.

(Continued)

OTHER PUBLICATIONS

Milas, Susanne M., et al., Acoustic Characterization of Microbubble Dynamics In Laser-Induced Optical Breakdown, IEEE Transactions on Ultrasonics, Ferroelectrics And Frequency Control, vol. 50, No. 5, May 2003, pp. 517-522.

(Continued)

*Primary Examiner*—Brian L. Casler
*Assistant Examiner*—James Kish
(74) *Attorney, Agent, or Firm*—Brooks Kushman P.C.

(57) ABSTRACT

An acoustic monitoring method and system in laser-induced optical breakdown (LIOB) provides information which characterize material which is broken down, microbubbles in the material, and/or the microenvironment of the microbubbles. In one embodiment of the invention, femtosecond laser pulses are focused just inside the surface of a volume of aqueous solution which may include dendrimer nanocomposite (DNC) particles. A tightly focused, high frequency, single-element ultrasonic transducer is positioned such that its focus coincides axially and laterally with this laser focus. When optical breakdown occurs, a microbubble forms and a shock or pressure wave is emitted (i.e., acoustic emission). In addition to this acoustic signal, the microbubble may be actively probed with pulse-echo measurements from the same transducer. After the microbubble forms, received pulse-echo signals have an extra pulse, describing the microbubble location and providing a measure of axial microbubble size. Wavefield plots of successive recordings illustrate the generation, growth, and collapse of microbubbles due to optical breakdown. These same plots can also be used to quantify LIOB thresholds.

37 Claims, 5 Drawing Sheets

U.S. PATENT DOCUMENTS

| | | | | |
|---|---|---|---|---|
| 5,749,364 | A | * | 5/1998 | Sliwa et al. ............... 600/438 |
| 5,810,731 | A | * | 9/1998 | Sarvazyan et al. .......... 600/438 |
| 6,165,440 | A | * | 12/2000 | Esenaliev ................. 424/1.11 |
| 6,471,968 | B1 | * | 10/2002 | Baker et al. ............. 424/280.1 |
| 6,546,272 | B1 | * | 4/2003 | MacKinnon et al. ........ 600/407 |

OTHER PUBLICATIONS

Milas, Susanne M., et al., Acoustic Detection of Microbubble Formation Induced By Enhanced Optical Breakdown of Silver/Dendrimer Nanocomposites, Applied Physics Letters, vol. 82, No. 6, Feb. 10, 2003, pp. 994-996.

O'Donnell, M., et al., Acoustic Detection of Laser Induced Optical Breakdown In Dendrimer Nanocomposites: Implications For Site Targeted Molecular Diagnostics An Therapeutics, IEEE Ultrasonic Symposium, Oct. 8-11, 2002, pp. 1961-1964.

Tomita, Y. et al., Behavior of Laser-Induced Caitation Bubbles in Liquid Nitrogen, Journal of Applied Physics; vol. 88, No. 10, Nov. 15, 2000, pp. 5993-6001.

Venugopalan, Vasan, et al., Role of Laser-Induced Plasma Formation n Pulsed Cellular Microsurgery and Micromanipulation, Physical Review Letter, vol. 88, No. 7, Feb. 18, 2002, pp. 078103-1-078103-4.

Noack, Joachim, et al., Influence of Pulse Duration on Mechanical Effects After Laser-Induced Breakdown in Water, Journal of Applied Physics, vol. 83, No. 12, Jun. 15, 1998, pp. 7488-7495.

Ye, Jing Yong, et al., Enhancement of Laser-Induced Optical Breakdown Using Metal/Dendrimer Nanocomposites, Applied Physics Letters, vol. 80, No. 10, Mar. 11, 2002, pp. 1713-1715.

Dayton, Paul A., et al., Optical An acoustical Dynamics of Microbubble Contrast Agents Inside Neutrophils, Biophysical Journal, vol. 80, Mar. 2001, pp. 1547-1556.

\* cited by examiner

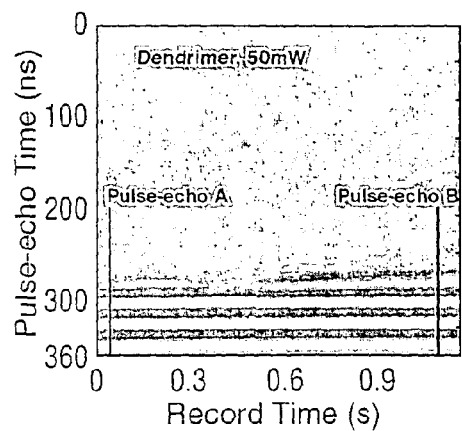
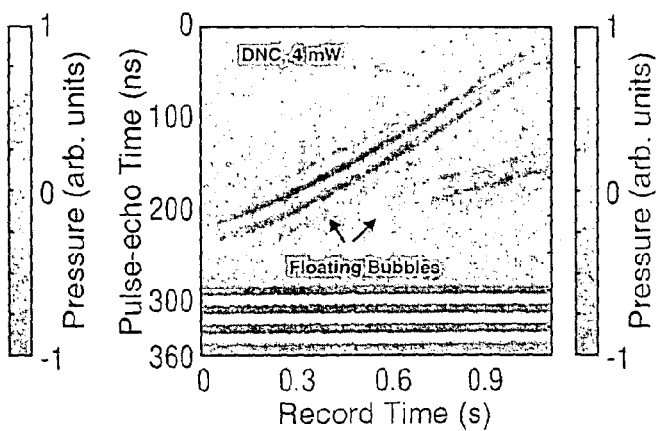
*Fig. 9a*  *Fig. 9b*
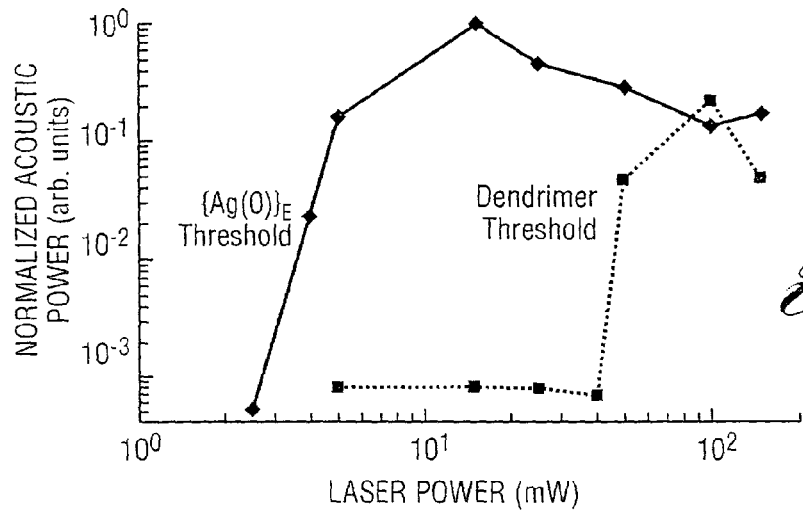
*Fig. 10*
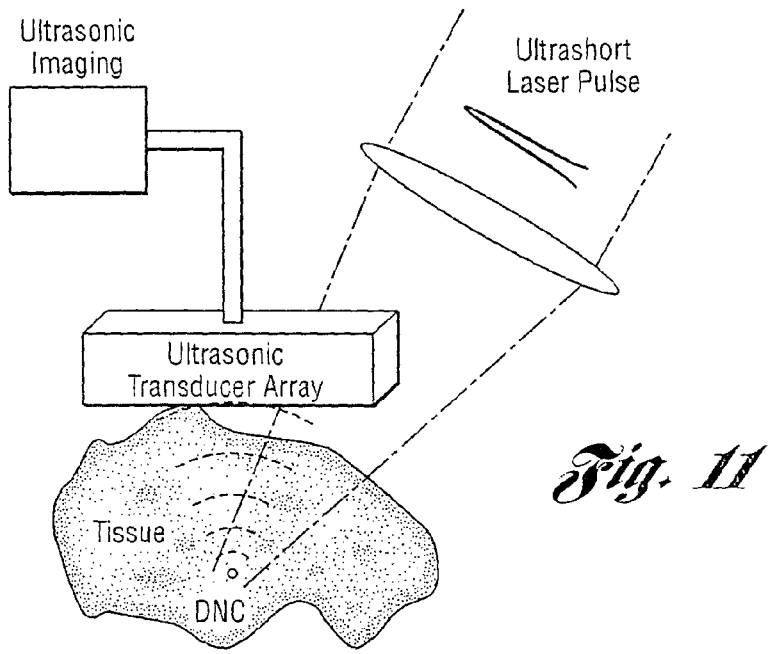
*Fig. 11*

ACOUSTIC MONITORING METHOD AND SYSTEM IN LASER-INDUCED OPTICAL BREAKDOWN (LIOB)

CROSS-REFERENCE TO RELATED APPLICATIONS

This application claims the benefit of U.S. provisional applications Ser. No. 60/407,018, filed Aug. 29, 2002, and Ser. No. 60/406,861, also filed on Aug. 29, 2002.

STATEMENT REGARDING FEDERALLY SPONSORED RESEARCH OR DEVELOPMENT

This invention was made at least in part with Government support under Contract Nos. NOI-CO-97111, HL47401, DK 47324 and HL67647 from the National Institutes of Health and Contract No. FG01-00NE22943 from the U.S. Department of Energy. The Government has certain rights to the invention.

BACKGROUND OF THE INVENTION

1. Field of the Invention

This invention relates to acoustic monitoring methods and systems in laser-induced optical breakdown (LIOB).

2. Background Art

Ultrafast lasers allow light to interact with materials in a femtosecond period, with peak powers many orders of magnitude higher than that of continuous wave light but with low average powers. Interestingly, an optically transparent material that has no linear absorption of incident laser light may have strong non-linear absorption under high intensity irradiation of a femtosecond pulsed laser. Non-linear absorption can lead to photodisruption of the material by generating a fast, expanding high-temperature plasma. Measurable secondary effects of the plasma include shock wave emission, temperature increases, and cavitation bubble generation. Many applications of ultrafast laser-induced optical breakdown (LIOB) have been developed recently, such as: micromachining of solid materials, microsurgery of tissues, and high-density optical data storage.

A number of methods have been developed to characterize LIOB. Stuart et al. determined LIOB via visual acquisition with Nomarski microscopy, which was simple but not well defined. Another approach for estimating breakdown threshold was to measure ablation depth using scanning electron microscopy (SEM). Furthermore, a combination of different microscopy techniques including optical microscopy, atomic force microscopy and SEM has been employed for accurate characterization of LIOB. However, none of these methods are real-time or applicable to liquid or liquid-like samples.

The dominant breakdown attributes studied in liquids are shock-wave emission and cavitation bubble generation. As a shock wave propagates spherically outward from the laser's focus, it dissipates energy and can be considered a broadband pressure wave after propagating only a few wavelengths from the source. Hence, pressure sensors can be strategically positioned within the liquid to record acoustic events associated with each optical breakdown. To observe cavitation bubble formation and subsequent behavior, laser-flash photography, optical limiting, and third-harmonic generation (THG) techniques are often employed. Each looks at a specific and limited facet of an optical breakdown.

U.S. Pat. Nos. 5,615,675 and 5,732,046 disclose opto-acoustic transducers for internally examining objects.

Laser-induced optical breakdown (LIOB) with femtosecond pulsed lasers is utilized in diverse applications, including biomedical systems, material characterization, and data storage. LIOB parameters and behavior have been investigated extensively. It occurs when sufficiently high threshold fluence is attained at the laser focus, inducing plasma formation. Plasma formation leads to non-linear energy absorption and measurable secondary effects that include shock-wave emission, heat transfer, and cavitation bubbles (i.e., photodisruption). The presence and magnitude of these breakdown attributes are used to determine a material's LIOB threshold.

U.S. Pat. No. 6,471,968 discloses a multi-functional nano device platform in the form of a dendrimer complex. Dendrimers are highly branched spherical macromolecules that provide templates for guest molecules to form dendrimer nanocomposite (DNC) particles. Optical limiting and third-harmonic generation techniques can explore some non-linear optical properties of these particles and their aggregates; yet they provide only limited information about the photodisruption.

SUMMARY OF THE INVENTION

An object of the present invention is to provide a method and system wherein a single molecule, or a small cluster of similar molecules, is transduced into a microbubble using laser-induced optical breakdown (LIOB) and detected using acoustic measurements on the microbubble, the material in which the microbubble is produced, or the microenvironment of the microbubble.

In carrying out the above object and other objects of the present invention, an acoustic monitoring method in laser-induced optical breakdown (LIOB) is provided. The method includes causing at least one acoustic wave associated with a microbubble to propagate in a volume of material. The method further includes detecting the at least one acoustic wave to obtain at least one signal. The method still further includes processing the at least one signal to obtain information which characterizes the material, the microbubble in the material or a microenvironment of the microbubble.

The information may quantify concentration of the additive.

The information may quantify concentration of a molecular agent transduced into a microbubble by the action of LIOB.

A single molecule of the additive may be detected.

The information may characterize the mechanical microenvironment of the microbubble.

The information may characterize the viscoelasticity of the microenvironment.

The information may characterize microbubble size.

The microbubble size may be determined using non-linear acoustic scattering from the microbubble.

The at least one acoustic wave may include at least one acoustic wave reflected from the microbubble.

The at least one reflected acoustic wave may include an ultrasound wave.

The at least one acoustic wave may include an acoustic shock wave which propagates outwardly from an LIOB site and defines an acoustic point source.

The point source may be determined by location of an additive in the material and the additive may enhance an electric field in the vicinity of the additive.

The information may characterize a photodisruption threshold of the material with the additive which is substantially lower than a photodisruption threshold of the material without the additive.

The material may include at least one nanodevice having the additive and a linked therapeutic agent and the at least one laser pulse may cause the at least one nanodevice to release the linked therapeutic agent into the microenvironment.

The information may characterize therapeutic efficacy of the therapeutic agent in the microenvironment.

The material may have an additive incorporated therein and the point source may be a desired point source substantially smaller than a point source defined by a microbubble created within the material without the additive.

The additive may include metal nano particles or domains.

The microbubble may be produced by at least one laser pulse which may be a focused laser pulse.

The microbubble may be produced by at least one ultrafast laser pulse.

The information may characterize a photodisruption threshold of the material.

The information may characterize location of the microbubble within the material.

The information may characterize microbubble behavior in the material.

The material may include a liquid or semi-liquid material, such as biological tissue.

The microbubble may be LIOB-induced and the acoustic shock wave defines position of the LIOB-induced microbubble which acts as an acoustic reflector.

The information may include an acoustic image of the material.

The method may further include time reversing the acoustic shock wave to form an acoustic image of the material.

Further in carrying out the above object and other objects of the present invention, an acoustic monitoring system in laser-induced optical breakdown (LIOB) is provided. The system includes means for causing at least one acoustic wave associated with a microbubble to propagate in a volume of material. The system further includes an acoustic wave detector for detecting the at least one acoustic wave to obtain at least one signal. The system still further includes means for processing the at least one signal to obtain information which characterizes the material, the microbubble in the material or a microenvironment of the microbubble.

The at least one acoustic wave may include at least one acoustic wave reflected from the microbubble and wherein the means for causing includes an acoustic source for directing acoustic energy to the material so that at least one acoustic wave propagates through the material to the microbubble to obtain the at least one reflected acoustic wave.

The at least one acoustic wave may include an acoustic shock wave which propagates outwardly from an LIOB site which defines an acoustic point source.

The system may further include a means for time reversing the acoustic shock wave to form an acoustic image of the material.

The above object and other objects, features, and advantages of the present invention are readily apparent from the following detailed description of the best mode for carrying out the invention when taken in connection with the accompanying drawings.

BRIEF DESCRIPTION OF THE DRAWINGS

FIG. 9a is a wave-field plot of dendrimer solution irradiated with 50 mW laser pulses (260 mJ/cm$^2$ per pulse); when the laser is unblocked (time origin approximates shutter opening), a bubble forms, adheres to the tank bottom, and grows; the location of the two pulse-echoes from FIGS. 8a and 8b are noted;

FIG. 9b is a wave-field plot of $\{Ag(O)\}_E$ DNC solution irradiated with 4 mW laser pulses (21 mJ/cm$^2$ per pulse); when the laser is unblocked, a bubble forms and floats upward toward the transducer; around 0.6 seconds, a second bubble forms and also travels upward; each liquid has slightly different acoustical properties, resulting in different sound propagation speeds within the liquid; to accommodate this, longer data records (around 20 ns) were acquired for measurements in $\{Ag(O)\}_E$ solutions than in pure dendrimer;

FIG. 10 is a graph of normalized average acoustic power vs. laser power; LIOB threshold values are marked for $\{Ag(O)\}_E$ DNC and PAMAM dendrimer; 4 mW (21 mJ/cm$^2$ per pulse) and 50 mW (260 mJ/cm$^2$ per pulse), respectively; and FIG. 11 is a schematic view showing high-resolution ultrasonic imaging and characterization using a point source generated from LIOB in DNC.

DETAILED DESCRIPTION OF THE PREFERRED EMBODIMENT(S)

Figure 1:
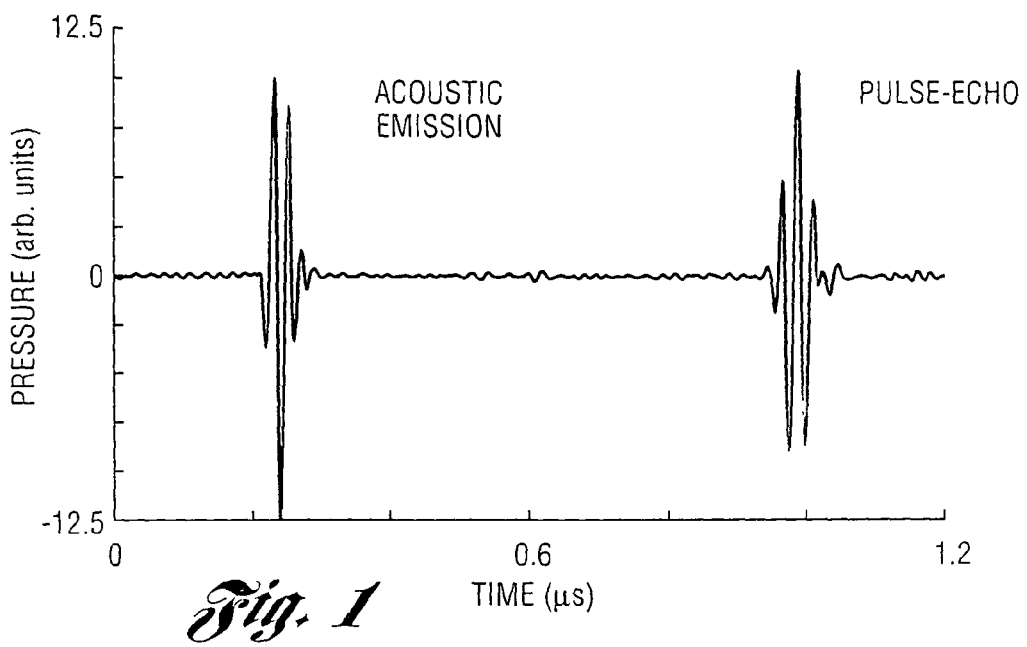
FIG. 1 is a graph which shows synchronized acoustic emission and pulse-echo measurement.

One aspect of the present invention provides an acoustic technique, based on pulse-echo measurements, to probe LIOB-induced microbubbles. It complements traditional methods in which shock wave generation is monitored in the far field of the source with an ultrasonic transducer. FIG. 1 presents a typical acoustic recording from an LIOB event in water where two acoustic signals are clearly detected. This experiment was performed with femtosecond pulsed Ti:Sapphire laser source and a PVDF ultrasonic recording system similar to the one described below. The first signal is a broadband pulse resulting from the initial shock wave (i.e., acoustic emission). The second signal is a pulse-echo recording from the LIOB site. The acoustic pulse was timed to arrive at this site about 750 nsec after the laser pulse, and the resultant reflected signal at this time signifies that a cavitation bubble was formed.

Once microbubble formation is detected, pulse-echo recordings with high frequency, high repetition rate ultrasound can monitor bubble dynamics with great sensitivity. Both linear and non-linear acoustic scattering measurements can be performed on the bubble to estimate its size and mechanical environment (e.g., viscoelastic constants). Moreover, performing scattering measurements as a function of time can help monitor changes in characteristics related to both diffusional and convective forces (e.g., forced bubble oscillations). As described herein below, pulse-echo recordings from an LIOB site in liquids are used primarily to determine the LIOB threshold of the material. These same measurements, however, also illustrate the ability of high frequency ultrasound to observe the dynamic process of microbubble generation, growth, and collapse, and to measure bubble size with submicron resolution.

Methods

Figure 2A:
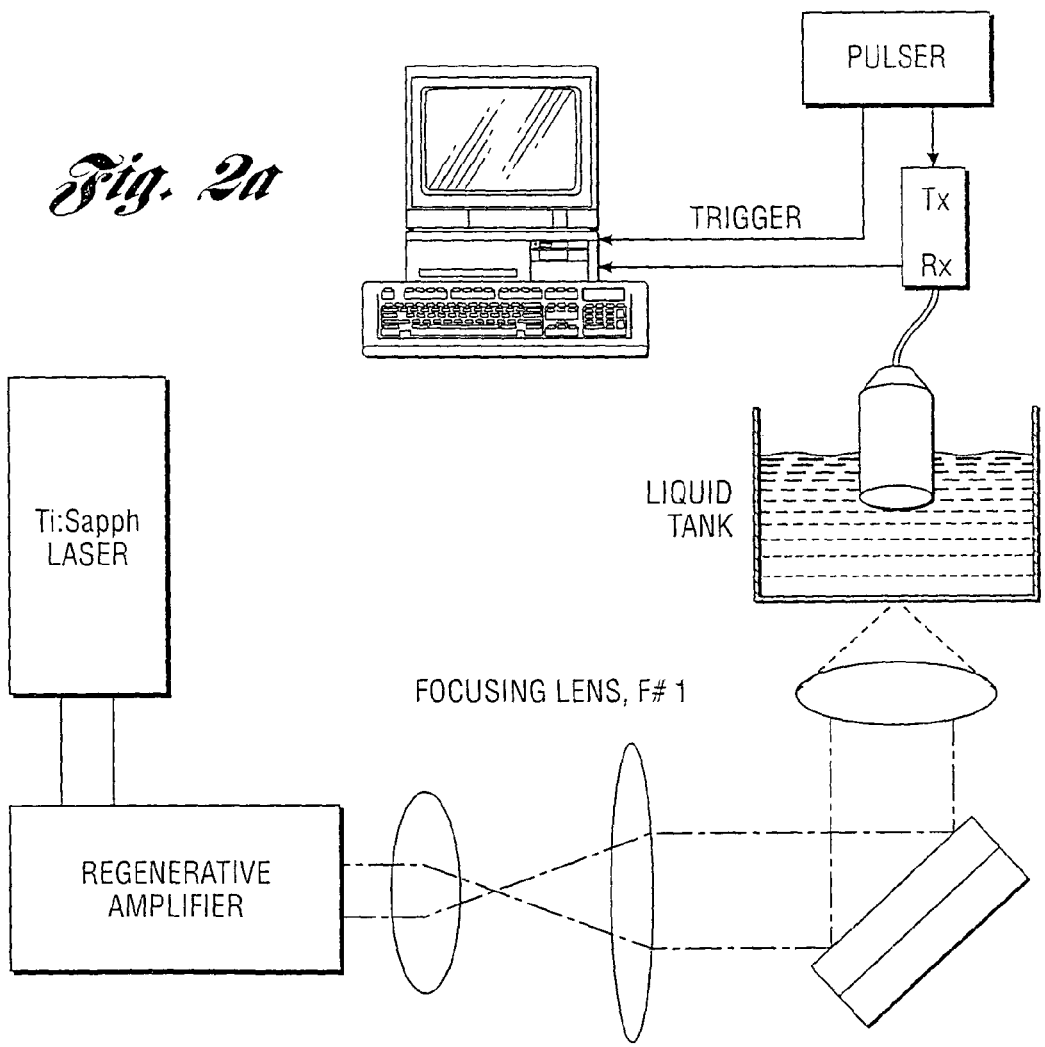
FIG. 2a is a schematic view of an integrated optical and acoustic experiment set-up.
Figure 2B:
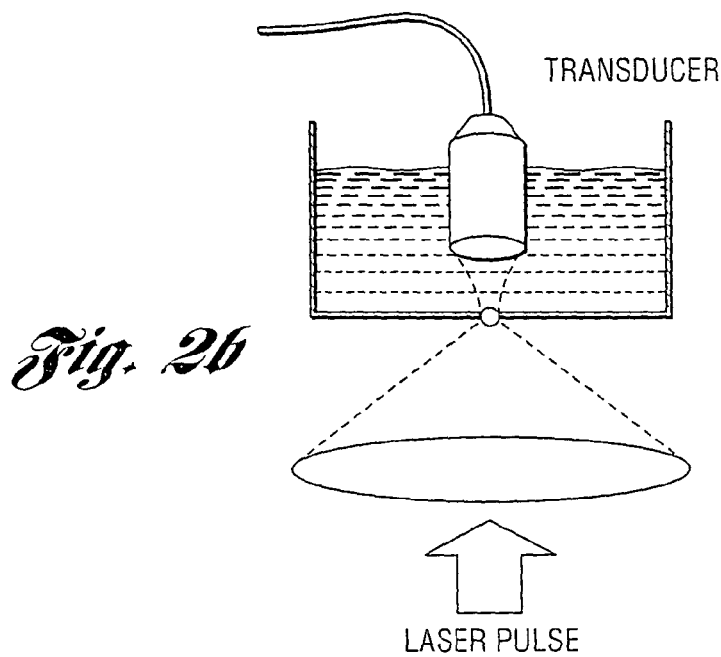
FIG. 2b is a schematic view which illustrates optical and acoustic alignment for an experiment set-up; laser pulses are focused at the inside surface of a tank's bottom; a transducer is aligned axially and laterally to this focus.

The optical source may be a 250-kHz regeneratively amplified Ti:Sapphire laser ($\lambda$=793 run) producing approximately 100 femtosecond pulses. The source is focused (10 µm diameter spot size) just inside the surface of a small water tank under THG guidance. Next, a tightly focused, single-element ultrasonic transducer (center frequency 60 MHz, 4.1 mm focal depth, 3 mm diameter) is positioned so its focus coincides axially and laterally with the laser focus. FIG. 2a illustrates the overall experimental set-up. The transducer and laser path are in series, and their foci are aligned within a few µm, as illustrated in FIG. 2b. A bottom surface of the tank is the focal plane for both the laser and the ultrasound transducer.

When breakdown occurs, the transducer detects a broadband pressure wave representing an acoustic emission from the LIOB site. In addition, the transducer is excited with an impulse (with a repetition rate of 2.44 kHz) to transmit and receive an acoustic pulse (i.e., pulse-echo) probing the liquid environment. The transducer output is amplified, filtered to match the electrical passband of the transducer, and digitized using an 8500 Gage board data acquisition system operating at a sample rate of 500 MHz. If a cavitation bubble forms from photodisruption, the signal will have a pulse (i.e., reflection) from the top surface of the bubble and a pulse from the tank bottom if either acoustic attenuation by the bubble is small or the acoustic focal spot is larger than the bubble size. The time difference between these two pulses is an acoustic shift on the order of nanoseconds. Hence by viewing acoustic shifts in consecutive pulse-echo recordings (i.e., wavefield plots), the formation and subsequent behavior of cavitation bubbles can be monitored.

As described above, previous investigators have monitored photodisruptions via acoustic emissions. This approach captures only bubble creation and eventual bubble collapse; however, the dynamic behavior of the bubble is unavailable. That is why acoustic pulse-echo monitoring is significant. Regardless of the liquid's transparency, the creation and behavior of cavitation bubbles can be clearly observed via acoustic pulse-echoes. Moreover, the two acoustic approaches can be combined. One can listen for the acoustic emission signifying microbubble generation, and at the same time, monitor the bubble environment through pulse-echo recordings. Both acoustic recordings are available during LIOB.

Once formed, three behaviors are observed for each cavitation bubble. It can remain in the liquid and float upward. It can adhere to the surface of the tank, become temporarily stationary, and grow as subsequent laser pulses are applied. Or it can collapse; this event is not always observed due to relatively long bubble lifetimes. These three behaviors are best illustrated through wavefield plots, as presented herein below.

Results

Figure 3A:
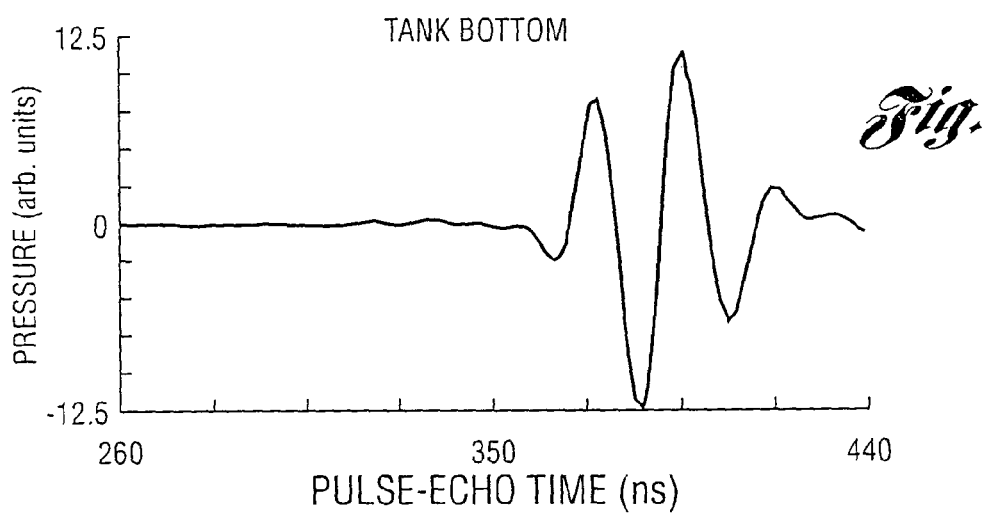
FIGS. 3a and 3b are graphs which show two acoustic pulse-echoes from water irradiated with laser pulses at LIOB threshold; the pulse-echo of FIG. 3a is a reflection from only the tank bottom before the laser pulse is applied; the pulse-echo of FIG. 3b shows the formation of a bubble after the laser pulse is applied.
Figure 3B:
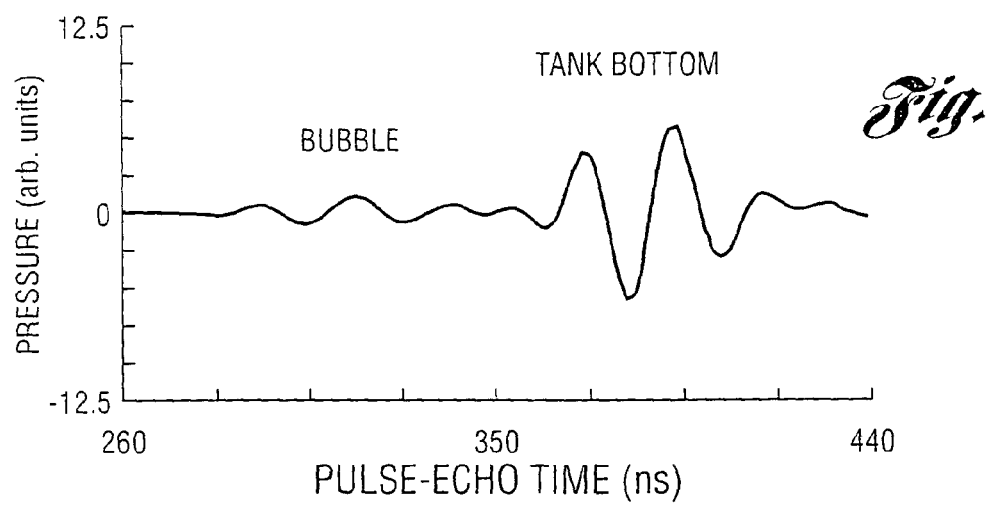

Each data record starts with the laser blocked by a shutter; hence initial pulse-echo signals are merely reflections from the tank's bottom. Within a few milliseconds, the shutter opens completely and the effects of the applied laser pulses are observed. If the laser power is below threshold, no bubble formation is recorded and consecutive pulse-echo recordings remain congruent. However, if the laser power is above threshold, acoustic shifts occur. Using this technique, distilled water's LIOB threshold was determined to be at an average laser power of 250 mW (1.3 J/cm$^2$ per pulse) for the present optical system, a value consistent with previous, non-acoustic measurements. FIGS. 3a and 3b show two pulse-echo signals from this data record; FIG. 3a illustrates laser blockage and the second bubble growth. By comparing these signals, a 70 ns shift is noted, corresponding to a 52.5 µm diameter bubble.

Figure 4:
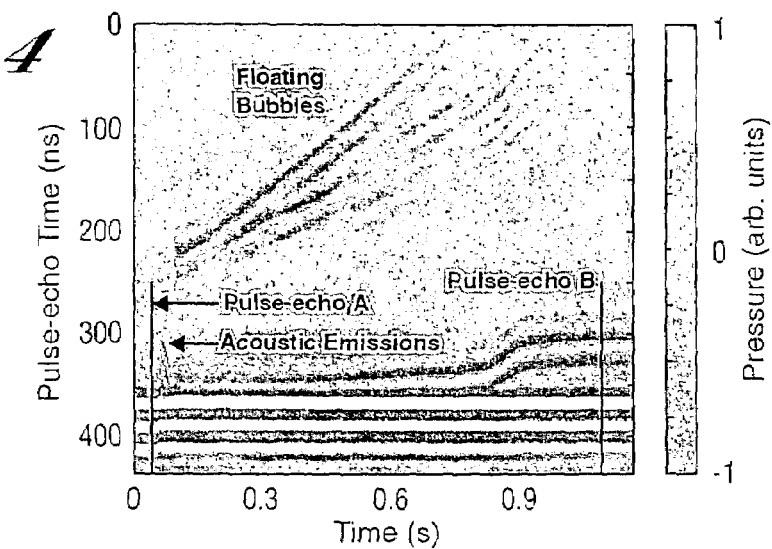
FIG. 4 is a wave-field plot of water irradiated with laser pulses at LIOB threshold; signals shown in FIGS. 3a and 3b are taken from locations marked, "pulse-echo A" and "pulse-echo B," respectively; black and white horizontal stripes near the bottom of the figure indicate successive reflected signals from the tank bottom; near the beginning of the record some acoustic emission signals show as random black and white pixels with amplitudes well above the background; pulse-echo signals from bubbles are non-horizontal black and white stripes indicating their positions change with time.

A wavefield plot taken at water's LIOB threshold illustrates the dynamic events of breakdown. FIG. 4 presents 2700 consecutive pulse-echo recordings that clearly show microbubble generation, where white corresponds to positive pressure, black to negative pressure, and mid-gray to no pressure in this and all subsequent wavefield plots. Each recording is 440 ns long, triggered by the transducer's pulser (repetition rate is 2.44 kHz). Initially, only the reflection from the tank bottom is observed. Once the laser is unblocked, noticeable changes occur. There are several acoustic emissions representing photodisruptions; and then several bubbles appear. Some remain in the liquid and float upward. Moreover, at least one bubble adheres to the tank's bottom and remains stationary while experiencing some growth as additional laser pulses are applied. Based on these recordings, a SNR value of 45 dB was calculated, translating to an approximately 7.5 precision in determining bubble diameter.

Figure 5:
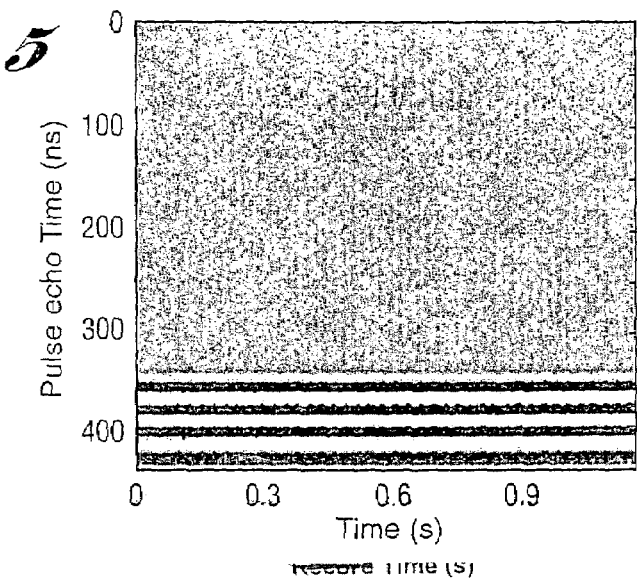
FIG. 5 is a wave-field plot of water irradiated with laser pulses below LIOB threshold; black and white horizontal stripes indicate successive reflected signals from the tank bottom; the uniform gray area shows no bubbles are produced or detected, as is expected.

By observing wave-field plots for average laser powers below and above 250 mW, water's LIOB threshold is confirmed and further bubble behavior is elucidated. FIG. 5 is a wave-field plot recorded with an average laser power of 50 mW (260 mJ/cm$^2$ per pulse). As expected for sub-threshold levels, no photodisruption events are detected.

Figure 6:
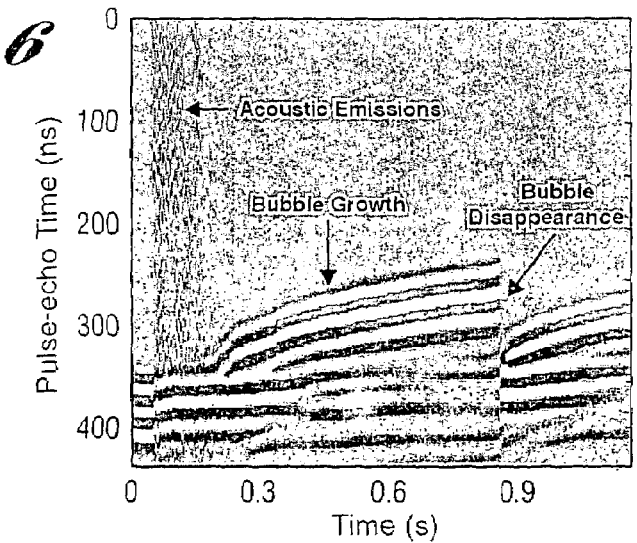
FIG. 6 is a wave-field plot of water irradiated with laser pulses well above the LIOB threshold; acoustic emissions are observed as random black and white pixels when the shutter initially opens; the curved black and white bands indicate pulse-echo monitoring of bubble growth; the bubble disappears as shown by the termination of these bands.

In contrast, FIG. 6 is a wave-field plot recorded with an average laser power of 450 mW (2.4 J/cm$^2$ per pulse), and exhibits substantial bubble behavior. Within this plot, there are numerous acoustic emissions observed prior to a bubble's adherence to the tank's bottom. Once a bubble adheres, acoustic emissions are not observed because each additional laser pulse reaches the bubble and promotes its growth. After a finite period, this bubble disappears, corresponding to bubble collapse. As soon as this happens, another bubble forms, adheres to the surface, and grows with time. It is hypothesized that the quickness of this bubble's formation and adherence is due to seeding of a nucleation site; i.e., when a bubble collapses it leaves a nucleation site primed for quick bubble formation.

Figure 7:
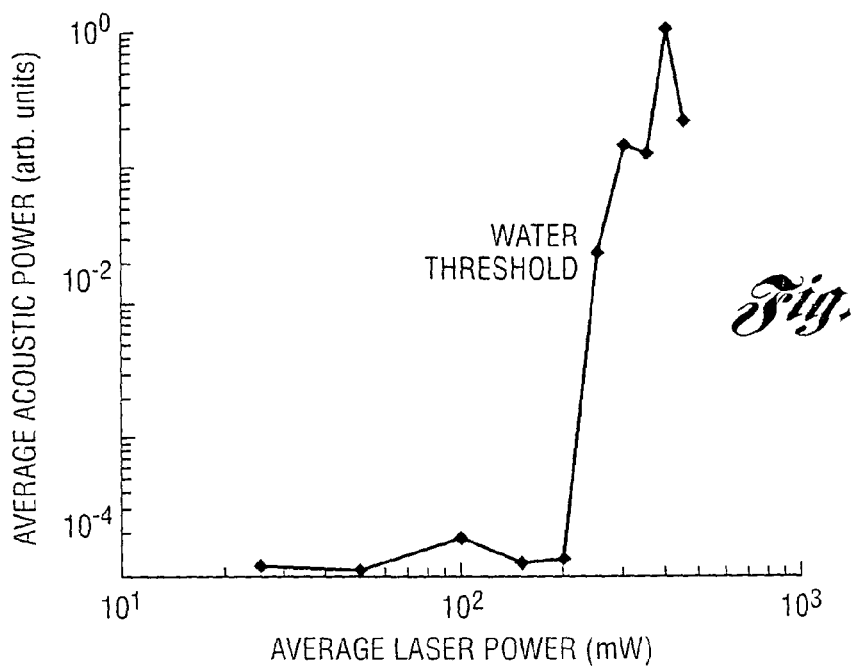
FIG. 7 is a graph of average acoustic power (normalized to largest value) vs. average laser power; the LIOB threshold value is marked for water at 250 mW (1.3 J/cm$^2$ per pulse)

The response to average laser powers ranging from 25 mW to 450 mW (130 mJ/cm$^2$ to 2.4 J/cm$^2$ per pulse) was characterized. For laser powers below 250 mW, no acoustic emissions or pulse-echo signals were observed. Only at and above this value were photodisruption events measured, all with final acoustic shifts over 60 ns (i.e., bubbles with a diameter of at least 45 μm). In addition, the average acoustic power of the pulse-echo signal corresponding to the reflection from the top of the bubble was calculated as the sum of the squared amplitude, averaged over time. The difference in average acoustic power between non-breakdown and breakdown events is at least two orders of magnitude. FIG. 7 shows this relationship. At high laser powers, acoustic shadowing due to multiple bubble generation accounts for the slight fluctuations in measured acoustic power.

Discussion

As previously mentioned, acoustic emissions associated with photodisruption provide information about the breakdown process. A complementary acoustic method using pulse-echo recordings is provided herein to monitor cavitation bubble creation, growth, and collapse. Bubble dynamics can be measured with precision using high-frequency ultrasound, where the accuracy of bubble size measurements can reach about 5 nm with the current system. More detailed acoustic scattering measurements as a function of frequency and intensity (non-linear effects) given precise bubble dimensions can help extract the viscoelastic properties of the acoustic medium surrounding the bubble.

For example, the present invention may also be used to measure tissue elastic properties using acoustic radiation force on laser-generated microbubbles. For example, an acoustic radiation force may be applied to microbubbles generated by laser-induced optical breakdown (LIOB) to study the mechanical response of the surrounding medium. The technique of applying acoustic radiation force to microbubbles seems well suited to many applications in cell biology as well as medical procedures. For example, it may monitor changes in intraocular lens elasticity during a potential presbyopia treatment involving LIOB. While traditional elasticity imaging and more recent techniques involving acoustic radiation force would be confounded by the limited speckle pattern in the lens, application of acoustic radiation force to microbubbles generated by LIOB would not have such limitations. Optical breakdown occurs when sufficiently high threshold fluence is attained at the focus of femtosecond pulsed lasers, including plasma formation and microbubble generation. LIOB microbubbles are of particular interest because they can be generated at very precise locations and optical parameters can be varied to control size.

Femtosecond laser pulses (700 fs) were focused in the volume of gelatin phantoms of varying concentration to form microbubbles. A two-element ultrasonic transducer generates acoustic radiation force on individual microbubbles while monitoring their displacement within an elastic medium. Gelatin phantoms with concentrations of 5%, 7.5% and 10% are used to compare the displacement of individual microbubbles in response to 1.5 MHz focused ultrasound by the outer element. Two types of acoustic excitation have been investigated: 1) single bursts ranging from 33 μsec to 200 ms; and 2) pulsed bursts at 1.22 kHz. The inner element receives pulse-echo recordings before, during and after the excitation bursts and correlation processing is performed offline to monitor microbubble position. Maximal microbubble displacements of 330 μm, 124 μm, and 48 μm have been measured in response to pulsed excitation in 5%, 7.5% and 10% gelatin phantoms, respectively. Alternatively, maximal microbubble displacements of 423 μm, 140 μm, and 60 μm have been measured in response to a single 6.7 ms ultrasound burst in 5%, 7.5% and 10% gelatin phantoms, respectively. These results demonstrate that microbubble displacement induced by acoustic radiation force is directly related to the gelatin concentration and, therefore, the elasticity of the surrounding medium.

In addition, carefully timed synchronizing pulse excitations so that the acoustic probe pulse coincides with LIOB-induced acoustic emissions can further characterize the bubble's mechanical environment. These methods may be especially important for fundamental cell biology studies in which a high numerical aperture, fs-pulsed laser system can create a 1 μm or less diameter cavitation bubble within the cytosol of a functioning cell.

As described in greater detail herein below, this method may be used to explore LIOB thresholds in two non-transparent aqueous solutions of potential biological significance: ethylenediamine core, polyamidoamine dendrimers and its silver-dendrimer hybrid nanocomposite (DNC). Dendrimers are highly branched three-dimensional macromolecules that provide scaffolding for guest molecules. When metallic guests are incorporated, enhanced electric fields established around the particles may significantly reduce the energy required for breakdown. The pulse-echo method presented here quantified the expected significant reduction in LIOB threshold when DNC particles were introduced to the environment. DNC particles have the potential for molecular therapeutics, where acoustic monitoring of site-specific photodisruption can validate therapeutic efficacy.

Through pulse-echo measurements, LIOB-induced bubble formation, growth, and collapse were observed and quantified. These parameters can be measured regardless of the liquid's optical transparency, providing a strong advantage over optical methods in non-transparent media. The average acoustic power of the records can also be calculated, providing a quantifiable measure of optical breakdown. Hence, the acoustic method presented here offers enhanced real-time measurement of photodisruption events, LIOB threshold quantification, as well as a means of detecting single molecules and characterizing the mechanical microenvironment of the resultant microbubble.

As previously mentioned, another aspect of the present invention provides a real-time acoustic technique for enhanced characterization of LIOB thresholds in various liquids, and its application to the study of DNC-enhanced breakdown. Femtosecond laser pulses, produced by a 250-kHz regeneratively amplified Ti:Sapphire laser ($\lambda$=793 nm), are directed into a small 2 ml liquid tank. The laser focus (10 μm diameter spot size) is positioned using third-harmonic generation (THG) measurements at the tank's bottom inside surface. When sufficiently intense laser pulses are applied to this interface, non-linear absorption ablates a localized volume, i.e., a photodisruption occurs. In the present technique, a tightly focused single-element ultrasonic transducer (center frequency 50 MHz, 4.1 mm focal depth, 3 mm diameter) is positioned such that its focus coincides axially and laterally with this laser focus.

During photodisruption a bubble forms, resulting in a high velocity shockwave that propagates spherically outward from the effective point source. After traveling a few wavelengths from the source, this wave can be considered a broadband pressure wave propagating toward the transducer, i.e., an acoustic emission. To characterize the bubble, the tank's bottom surface is actively pulsed via pulse-echo measurements from the same transducer. If a bubble forms, the signal will have a pulse (i.e., reflection) from the top surface of the bubble and a pulse from the tank bottom (if either acoustic attenuation by the bubble is small or the acoustic focal spot is larger than the bubble size). The time difference between these pulses is quantified as an acoustic shift on the order of nanoseconds (ns). By viewing acoustic shifts in consecutive pulse-echoes (i.e., wave-field plots), cavitation bubble formation and subsequent behavior can be visualized.

The two aqueous solutions evaluated were pure ethylenediamine (EDA) core poly(amidoamine) (PAMAM) dendrimers and a silver-dendrimer hybrid nanocomposite, (\{(Ag(O)$_{97}$-PAMAM_E5.5COOAg\}) (\{Ag(O)\}$_E$: for short). A carboxyl terminated, generation 5.5 poly(amidoamine) dendrimer served as a template for the silver nanocomposite. After optical alignment, the acoustical tank was filled with the test liquid while laser pulses were blocked with a mechanical shutter. Each data record consisted of opening the shutter and recording approximately one second of pulse-echo signals (2700 consecutive recordings). Each recording was 360 ns long, triggered by the transducer's pulser with a repetition rate of 2.44 kHz. Acoustic emissions can occur on each laser firing (250 kHz repetition rate); however the recording of these signals was not synchronized with the pulse-echo data reported here.

Wave-field plots of consecutive pulse-echo recordings enable one to observe bubble formation and behavior directly. While the mechanical shutter blocks the laser pulses, the pulse-echo signal simply represents an acoustic reflection from the tank bottom. This signal persists when the laser is unblocked if its power lies below the liquid's LIOB threshold. Once threshold is attained, significant changes are observed. The presence of additional acoustic reflections is used for threshold estimates.

Figure 8A:
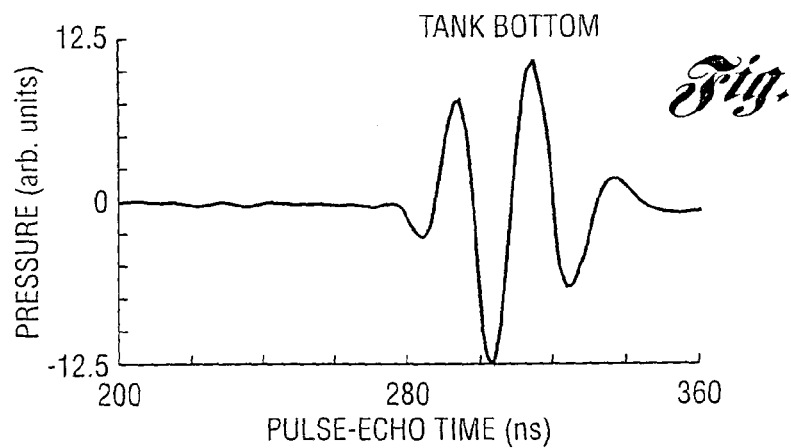
FIGS. 8a and 8b are graphs showing two pulse-echoes from pure dendrimer solution irradiated with 50 mW laser pulses (260 mJ/cm$^2$ per pulse); the pulse-echo of FIG. 8a is a reflection from only the tank bottom before the laser pulse is applied; the pulse-echo of FIG. 8b shows the formation of a bubble after the laser pulse is applied; the acoustic shift is measured as the time between the second zero crossings of the two pulses in FIG. 8b; for this pulse-echo, a 34-ns shift is observed, corresponding to a 25.5 μm bubble.
Figure 8B:
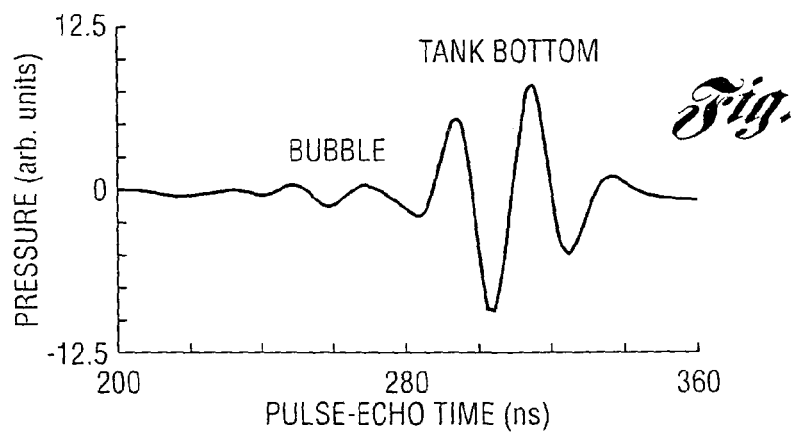

For a pure dendrimer aqueous solution, the optical threshold (average laser power) at which significant acoustic power is reflected from a microbubble was found to be 50 mW (260 mJ/cm$^2$ per pulse). FIGS. 8a and 8b show two pulse-echo recordings taken at the dendrimer's threshold power level; FIG. 8a illustrates laser blockage and FIG. 8b is during bubble growth. By comparing these lines, it is clear that a bubble has formed with a 34 ns acoustic shift, corresponding to a 25.5 μm bubble.

FIG. 9a is a wave-field plot illustrating this bubble's formation and adherence to the tank surface. Initially, only the reflection from the tank bottom is observed, corresponding to laser blockage. When the bubble forms, a new acoustic pulse emerges above this reflection and gradually shifts toward the transducer. As time progresses, the shift increases, confirming bubble growth. The final extent of this shift provides a direct measure of axial bubble size.

An aqueous solution of \{Ag(O)\}$_E$ was characterized using the same procedure. The LIOB threshold determined acoustically for \{Ag(O)\}$_E$ is 4 mW (21 mJ/cm$^2$ per pulse), over an order of magnitude lower than the threshold of the pure dendrimer solution.

As noted above, for pure water a threshold of 250 mW (1.3 J/cm$^2$ per pulse) was obtained, more than 50 times higher than the threshold for the DNC solution. This result provides an unquestionable advantage of using DNC particles with a low threshold for photodisruption. FIG. 9b illustrates the acoustic events when the DNC solution is irradiated with laser pulses close to its LIOB threshold. Initially, no bubble is present. Once the shutter opens, two distinct cavitation events occur. The bubbles do not adhere to the tank surface as seen for pure dendrimer; instead they float upward toward the transducer. As bubbles move toward the transducer, they exit the transducer's 250 μm depth of field and pulse-echo measurements decrease in intensity.

A range of laser powers was investigated for each aqueous solution. For each laser power, the average reflected acoustic power from the top of the bubble was calculated as the sum of the squared amplitude, averaged over time. This provides a quantifiable measure of the average acoustic power associated with non-breakdown and breakdown events.

FIG. 10 shows the dramatic increase in average acoustic power for data records containing optical breakdowns. At high laser powers, acoustic shadowing due to bubble generation accounts for the slight decline in acoustic power. FIG. 10, furthermore, illustrates the ability to manipulate LIOB threshold values based on the solution's molecular attributes. This unlocks enormous potential in many applications. For instance, in biomedical systems, DNC particles can be biochemically targeted to sites where localized photodisruption can be induced, either releasing encapsulated therapeutics or ablating aberrant cells (such as cancer). Furthermore, cavitation bubbles resulting from photodisruption can be manipulated with either acoustic or optical sources for enhanced therapeutic effects, and probed with high frequency ultrasound to validate therapeutic efficacy and quantify the concentration of the therapeutic agent.

This new acoustic technique is capable of characterizing LIOB thresholds in solutions and semi-liquid materials such as soft tissue. This technique can be used to quantify the significant reduction in LIOB threshold when DNC particles are introduced to the environment.

Referring now to FIG. 11, the method and system of the present invention can be used for ultrasonic detection, imaging, and characterization of the breakdown region. For example, during optical breakdown a bubble forms, resulting in a high velocity shockwave that propagates spherically outward from the effective point source. Because the nanoparticle enhanced LIOB occurs initially starting from the immediate surrounding of the nanoparticles rather than the entire laser focal spot, one obtains a point ultrasonic source with much smaller size than that without metal nanoparticles. A pulse-echo imaging system can then probe this site with high resolution by time reversing the shock wave field detected by the imaging array, as shown in FIG. 11. This time reversal process produces a perfect focus, even at very high ultrasonic frequencies. The resolution of ultrasonic imaging is ultimately determined by the quality of the focus. Thus, one can achieve high resolution ultrasonic imaging with the enhanced LIOB using metal nanoparticles or metallic nanocomposites. In addition, using ultrasonic pulse-echo detection one can measure the microbubble size thus characterizing the breakdown region.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An acoustic monitoring method in laser-induced optical breakdown (LIOB) wherein an LIOB-induced microbubble is formed at an LIOB site, the method comprising the steps of:
   causing at least one acoustic wave reflected from the LIOB-induced microbubble at the LIOB site to propagate in a volume of material;
   detecting the at least one acoustic wave to obtain at least one signal from the LIOB site; and
   processing the at least one signal to obtain information which characterizes the material, the microbubble in the material or a microenvironment of the microbubble wherein the at least one acoustic wave includes an acoustic shock wave which propagates outwardly from an LIOB site and defines an acoustic point source wherein the point source is determined by location of an additive in the material wherein the additive enhances an electric field in the vicinity of the additive and wherein the information characterizes a photodisruption threshold of the material with the additive which is substantially lower than a photodisruption threshold of the material without the additive.

2. The method as claimed in claim 1, wherein the information characterizes microbubble size.

3. The method as claimed in claim 2, wherein microbubble size is determined using non-linear acoustic scattering from the microbubble.

4. The method as claimed in claim 1, wherein the at least one reflected acoustic wave includes an ultrasound wave.

5. The method as claimed in claim 1, wherein the acoustic shock wave defines position of the LIOB-induced microbubble which acts as an acoustic reflector.

6. The method as claimed in claim 1, wherein the information quantifies concentration of the additive.

7. The method as claimed in claim 6, wherein a single molecule of the additive is detected.

8. The method as claimed in claim 1, wherein the material includes at least one nanodevice having the additive and a linked therapeutic agent and wherein at least one laser pulse causes the at least one nanodevice to release the linked therapeutic agent into the microenvironment.

9. The method as claimed in claim 8, wherein the information characterizes therapeutic efficacy of the therapeutic agent in the microenvironment.

10. The method as claimed in claim 1, wherein the material has an additive incorporated therein and wherein the point source is a desired point source substantially smaller than a point source defined by a microbubble created within the material without the additive.

11. The method as claimed in claim 10, wherein the additive includes metal nano particles or domains.

12. The method as claimed in claim 1, wherein the microbubble is produced by at least one laser pulse.

13. The method as claimed in claim 12, wherein the at least one laser pulse includes a focused laser pulse.

14. The method as claimed in claim 1, wherein the information characterizes location of the microbubble within the material.

15. The method as claimed in claim 1, wherein the information characterizes microbubble behavior in the material.

16. The method as claimed in claim 1, wherein the material includes a liquid or semi-liquid material, such as biological tissue.

17. The method as claimed in claim 1, wherein the information includes an acoustic image of the material.

18. The method as claimed in claim 1, further comprising time reversing the acoustic shock wave to form an acoustic image of the material.

19. An acoustic monitoring system in laser-induced optical breakdown (LIOB) wherein an LIOB-induced microbubble is formed at an LIOB site, the system comprising:
   means for causing at least one acoustic wave reflected from the microbubble at the LIOB site to propagate in a volume of material;
   an acoustic wave detector for detecting the at least one acoustic wave to obtain at least one signal from the LIOB site; and
   means for processing the at least one signal to obtain information which characterizes the material, the microbubble in the material or a microenvironment of the microbubble wherein the at least one acoustic wave includes an acoustic shock wave which propagates outwardly from an LIOB site and which defines an acoustic point source wherein the point source is determined by location of an additive in the material wherein the additive enhances an electric field in the vicinity of the additive and wherein the information characterizes a photodisruption threshold of the material with the additive which is substantially lower than a photodisruption threshold of the material without the additive.

20. The system as claimed in claim 19, wherein the information characterizes microbubble size.

21. The system as claimed in claim 20, wherein the microbubble size is determined using non-linear scattering from the microbubble.

22. The system as claimed in claim 19, wherein the means for causing includes an acoustic source for directing acoustic energy to the material so that at least one acoustic wave propagates through the material to the microbubble to obtain the at least one reflected acoustic wave.

23. The system as claimed in claim 22, wherein the at least one reflected acoustic wave includes an ultrasound wave.

24. The system as claimed in claim 19, wherein the acoustic shock wave defines position of the LIOB-induced microbubble which acts as an acoustic reflector.

25. The system as claimed in claim 19, wherein the information quantifies concentration of the additive.

26. The system as claimed in claim 25, wherein a single molecule of the additive is detected.

27. The system as claimed in claim 19, wherein the material includes at least one nanodevice having the additive and a linked therapeutic agent and wherein at least one laser pulse causes the at least one nanodevice to release the linked therapeutic agent into the microenvironment.

28. The system as claimed in claim 27, wherein the information characterizes therapeutic efficacy of the therapeutic agent in the microenvironment.

29. The system as claimed in claim 19, wherein the material has an additive incorporated therein and wherein the point source is a desired point source substantially smaller than a point source defined by a microbubble created within the material without the additive.

30. The system as claimed in claim 29, wherein the additive includes metal nano particles or domains.

31. The system as claimed in claim 19, wherein the microbubble is produced by at least one laser pulse.

32. The system as claimed in claim 31, wherein the at least one laser pulse includes a focused laser pulse.

33. The system as claimed in claim 19, wherein the information characterizes location of the microbubble within the material.

34. The system as claimed in claim 19, wherein the information characterizes microbubble behavior in the material.

35. The system as claimed in claim 19, wherein the material includes a liquid or semi-liquid material, such as biological tissue.

36. The system as claimed in claim 19, wherein the information includes an acoustic image of the material.

37. The system as claimed in claim 19, further comprising means for time reversing the acoustic shock wave to form an acoustic image of the material.

* * * * *